(12) United States Patent
Alnawah

(10) Patent No.: US 11,731,951 B1
(45) Date of Patent: Aug. 22, 2023

(54) WATER REACTIVITY WITH NATURAL PRODUCTS

(71) Applicant: King Faisal University, Al-Ahsa (SA)

(72) Inventor: Jawaher Alnawah, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/117,579

(22) Filed: Mar. 6, 2023

(51) Int. Cl.
*C07D 311/94* (2006.01)
*C07D 311/96* (2006.01)

(52) U.S. Cl.
CPC .......... *C07D 311/94* (2013.01); *C07D 311/96* (2013.01)

(58) Field of Classification Search
CPC .................................................... C07D 311/94
USPC ......................................................... 549/280
See application file for complete search history.

(56) References Cited

U.S. PATENT DOCUMENTS

2012/0083527 A1    4/2012   Burkart et al.

OTHER PUBLICATIONS

Snider et al. Org Letts (2005) vol. 7(22): 4939-4941.*
Hans-Peter Fiedler, "Abyssomicins—A 20-Year Retrospective View", Mar Drugs. Jun. 2021; 19(6): 299. (May 24, 2021. doi: 10.3390/md19060299).
PubChem Compound #11573744, Oct. 26, 2006.

* cited by examiner

*Primary Examiner* — Taofiq A Solola
(74) *Attorney, Agent, or Firm* — Nath, Goldberg & Meyer; Richard C. Litman

(57) ABSTRACT

A novel abyssomicin analogue compound and method of synthesizing the novel abyssomicin analogue compound are provided. The synthesis method includes the novel abyssomicin analogue compound being simply produced from a mixture of water and a co-solvent with linear precursors. The water molecules in the synthesis method can have dual roles, which are cyclisation followed by hydration via a unique mechanism. Abyssomicins are a family of spirotetronate natural products exhibiting promising bioactivities.

14 Claims, No Drawings

WATER REACTIVITY WITH NATURAL PRODUCTS

BACKGROUND

1. Field

The disclosure of the present patent application relates to abyssomicin analogues and their synthesis methods.

2. Description of the Related Art

Abyssomicins are a family of spirotetronate natural products exhibiting promising bioactivities. The abyssomicin's biological activities inspire possible applications in medicinal chemistry and drug discovery.

Abyssomicins, their properties, reactions, and potential uses are known, and racemic analogues have been disclosed previously. For example, "Abyssomicins—A 20-Year Retrospective View", discloses that abyssomicin C and atropabyssomicin C show a high antibiotic activity against Gram-positive bacteria, including multi-resistant and vancomycin-resistant strains. Said multicyclic structures and related structures are shown in FIGS. 2, 4, and 5.

Also, US 2012/0083527 A1, to Burkart et al. relates generally to compositions and methods for treating cancer. In some aspects, novel spirohexenolides, and methods of using and producing them are described. Said spirohexenolides are related to abyssomicins and are multicyclic structures. Due to abyssomicin's biological activities that have possible applications in medicinal chemistry and drug discovery, it would be advantageous to obtain new such compounds and/or analogues, particularly if they could be formed in a simple manner.

SUMMARY

The presently disclosed subject matter relates to a novel organic abyssomicin analogue compound and a synthesis method which can include being simply produced from a mixture of water and a co-solvent with linear precursors rac-(6E,8E,10E)-1-(4-methoxy-5-methylene-2-oxo-2,5-dihydrofuran-3-yl)-3-methyldodeca-6,8,10-triene-1,5-dione. The water molecules, in this case, can serve dual purposes, which are cyclisation followed by hydration via a unique mechanism. The produced compound is interesting because of its stability for a long time with quite rigid structure, which can be of interest to medicinal chemists and pharmaceutical scientists due to possible biological activities that have possible applications in medicinal chemistry and drug discovery.

In one embodiment, the present subject matter relates to a novel organic abyssomicin analogue. The novel compound is rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate having the following structure:

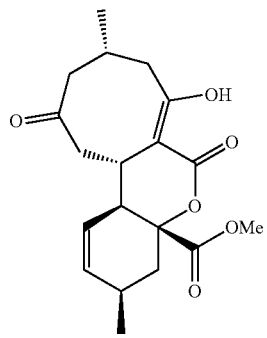 [SMILES: COC(=O)[C@@]12C[C@@H](C)C=C[C@H]1[C@@H]1CC(=O)C[C@H](C)C/C(O)=C\1C(=O)O2]

rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate In another embodiment, the present subject matter relates to a method for producing the novel organic abyssomicin analogue compound rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate, which includes being simply produced from a mixture of water and a co-solvent with linear precursors.

In an embodiment, rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate is abyssomicin analogue of the present subject matter, may be effective in a pharmaceutical or drug composition. The chemical structure of the synthesized analogues is interesting because of their stability with interesting stereochemistry, which can be of interest to medicinal chemists and pharmaceutical scientists.

An embodiment of the present subject matter is directed to a pharmaceutical composition including the abyssomicin analogue compound rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate and a pharmaceutically acceptable carrier.

An embodiment of the present subject matter is directed to a method of making a pharmaceutical composition including mixing the abyssomicin analogue compound rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of treating applicable diseases, including administering to a subject in need thereof a therapeutically effective amount of a pharmaceutical composition according to the present subject matter.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "racemic compounds", often abbreviated as rac, rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate, rac-(6E,8E,10E)-1-(4-methoxy-5-methylene-2-oxo-2,5-dihydrofuran-3-yl)-3-methyldodeca-6,8,10-triene-1,5-dione, etc. Racemic means composed of dextrorotatory and levorotatory forms of a compound in equal proportion. Dextrorotatory description (of a compound) means having the property of rotating the plane of a polarized light ray to the right, i.e., clockwise facing the oncoming radiation. Levorotatory description (of a compound) means having the property of rotating the plane of a polarized light ray to the left, i.e., counterclockwise facing the oncoming radiation. A racemic mixture, also called racemate, is a mixture of equal quantities of two enantiomers, or substances that have dissymmetric molecular structures that are mirror images of one another. Because enantiomers, a certain type of isomers, are mirror images, each enantiomer rotates plane-polarized light in an equal but opposite direction and is optically inactive. Racemic is often abbreviated as "rac".

The term "optional" or "optionally" means that the subsequently described event or circumstance may or may not occur and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The presently disclosed subject matter relates to a novel organic abyssomicin analogue compound and a synthesis method which includes being simply produced from a mixture of water and a co-solvent with linear precursors. The water molecules can serve dual purposes, which are cyclisation followed by hydration via a unique mechanism. During the investigations of the cyclisation step in the water of non-natural substrates, novel organic structures were observed. The resulting structure possesses a novel skeleton with a new core featuring fused 6/6/8 rings with quite rigid structure. The chemical structures are interesting because of their stability for a long time with interesting stereochemistry.

In one embodiment, the present subject matter relates to a novel organic abyssomicin analogue compound. The novel compound structure, rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate, possesses a novel skeleton with a new core featuring fused 6/6/8 rings with defined stereochemistry and having the following structure synthesized using known rac-(3E,6S,9E,10aS,13R,14aR)-15-methoxy-6,13-dimethyl-6,7,13,14-tetrahydro-2H-3,14a-(metheno)benzol[b][1]oxacyclododecine-2,4,8(5H,10aH)-trione:

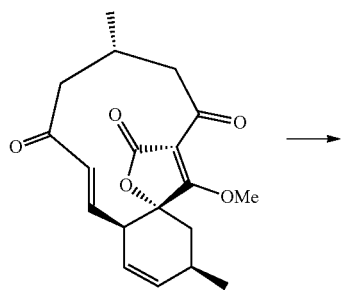

rac-
(3E, 6S, 9E, 10aS, 13R, 14aR)-
15-methoxy-6,13-dimethyl-6,7,13,14-
tetrahydro-2H-3,14a-
(metheno)benzo[b]
[1]oxacyclododecine-2,4,8
(5H, 10aH)-trione

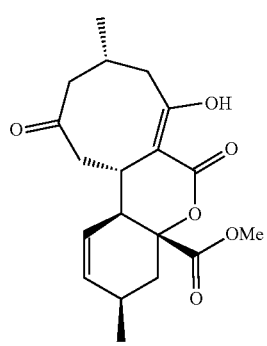 [SMILES: COC(=O)[C@@]12C[C@@H](C)C=C[C@H]1[C@@H]1CC(=O)C[C@H](C)C/C(O)=C\1C(=O)O2]

rac-methyl
(3S, 4aS, 9S, 12aR, 12bR, Z)-
7-hydroxy-3,9-
dimethyl-6,11-
dioxo-3,4,6,8,9,10,11,12,1
2a,12b-decahydro-4aH-
cycloocta[c]chromene-4a-
carboxylate In an embodiment, the present subject matter relates to a method of synthesizing a novel organic abyssomicin analogue compound having the structure

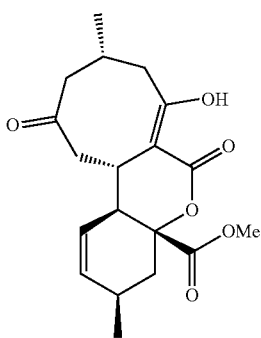

which is rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate.

In one embodiment, the present subject matter relates to a method of synthesizing an organic abyssomicin analogue compound rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate having the following structure

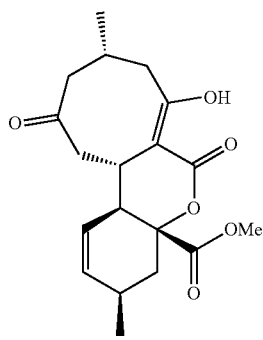

the method comprising the steps of:
dissolving substrate rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione having the following structure:

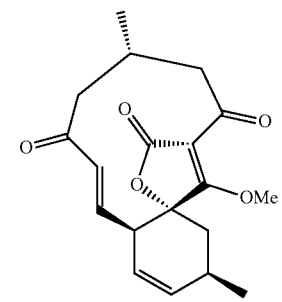

rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione in $H_2O$ and $CH_3CN$ to obtain a first mixture;
stirring the first mixture until the reaction complete;
quenching the reaction with organic solvent forming aqueous and organic layers;
extracting the aqueous layer with an organic solvent;
drying, filtering, and concentrating the combined organic extracts to produce a crude material; and
purifying the crude material to obtain hydration adduct rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate.

In certain embodiments in this regard, the first mixture can be stirred at room temperature for about one day. In other embodiments, the aqueous layer can be extracted with dichloromethane.

Once obtained, the organic extracts can be dried over $MgSO_4$, filtered, and concentrated in vacuo. Similarly, the crude material can be purified by flash column chromatography (20% ethyl acetate:petroleum ether), obtaining the hydration adduct rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate at an about 98% yield.

According to the present methods, the $H_2O$ can provide cyclisation followed by hydration.

In additional embodiments, the present subject matter relates to a method of synthesizing rac-(3E,6S,9E,10aS,13R,14aR)-15-methoxy-6,13-dimethyl-6,7,13,14-tetrahydro-2H-

3,14a-(metheno)benzo[b][1]oxacyclododecine-2,4,8(5H,10aH)-trione having the following structure:

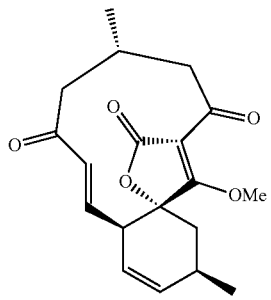

rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione the method comprising the steps of:
dissolving diketone rac-(6E,8E,10E)-1-(4-methoxy-5-methylene-2-oxo-2,5-dihydrofuran-3-yl)-3-methyldodeca-6,8,10-triene-1,5-dione in CHCl₃ to produce a reaction mixture;
purifying the reaction mixture to obtain a mixture of diastereomers rac-(3E,6S,9E,10aR,13S,14aS)-15-methoxy-6,13-dimethyl-6,7,13,14-tetrahydro-2H-3,14a-(metheno)benzol[b][1]oxacyclododecine-2,4,8(5H,10aH)-trione and rac-(3E,6S,9E,10aS,13R,14aR)-15-methoxy-6,13-dimethyl-6,7,13,14-tetrahydro-2H-3,14a-(metheno)benzol[b][1]oxacyclododecine-2,4,8(5H,10aH)-trione;
separating the mixture of diastereomers rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione and rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione;
isolating minor isomer rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione; and
isolating major isomer rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione, wherein the synthesis of rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione is represented by the following general reaction:

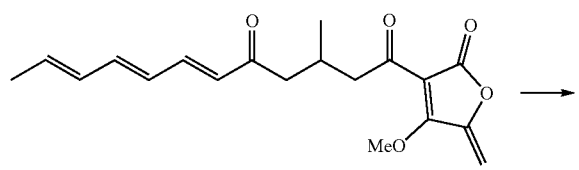

rac-(6E, 8E, 10E)-1-(4-methoxy-5-methylene-2-oxo-2,5-dihydrofuran-3-yl)-3-methyldodeca-6,8,10-triene-1,5-dione

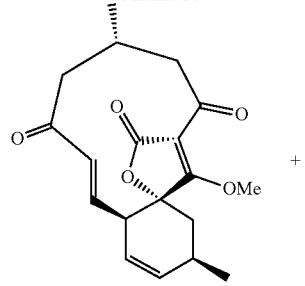

rac-(3E, 6S, 9E, 10aS, 13R, 14aR)-15-methoxy-6,13-dimethyl-6,7,13,14-tetrahydro-2H-3,14a-(metheno)benzo[b][1]oxacyclododecine-2,4,8(5H, 10aH)-trione

+

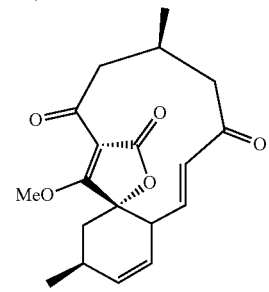

rac-(3E, 6S, 9E, 10aR, 13S, 14aS)-15-methoxy-6,13-dimethyl-6,7,13,14-tetrahydro-2H-3,14a-(metheno)benzo[b][1]oxacyclododecine-2,4,8(5H, 10aH)-trione In this regard, the dissolved diketone rac-(6E,8E,10E)-1-(4-methoxy-5-methylene-2-oxo-2,5-dihydrofuran-3-yl)-3-methyldodeca-6,8,10-triene-1,5-dione in CHCl₃ can be refluxed for about 2 days. Further, the reaction mixture can be purified by flash column chromatography, while the mixture of diastereomers rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione and rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione are separated by HPLC. Following this process, the minor isomer rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione can be isolated at an about 20% yield, while the major isomer rac-(3E,6S,9E,10aS,13R,14aR)-15-methoxy-6,7,13,14-tetrahydro-2H-3,14a-(metheno)benzo[b][1]oxacyclododecine-2,4,8(5H,10aH)-trione can be isolated at an about 67% yield.

One exemplary process for the synthesis of rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate is as follows: Diketone rac-(6E,8E,10E)-1-(4-methoxy-5-methylene-2-oxo-2,5-dihydrofuran-3-yl)-3-methyldodeca-6,8,10-triene-1,5-dione was dissolved in CHCl₃ and refluxed for 2 days. The reaction mixture was then purified by flash column chromatography to give a mixture of rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione and rac-(3E,6S,9E,10aR,13S,14aS)-15-methoxy-6,13-dimethyl-6,7,13,14-tetrahydro-2H-3,14a-

(metheno)benzo[b][1]oxacyclododecine-2,4,8(5H,10aH)-trione in a quantitative yield. The diastereomers were further separated by HPLC. Minor isomer rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione was isolated as a yellow oil in 20% yield, and major isomer rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione was isolated as a yellow-orange oil in 67% yield represented by the following general reaction:

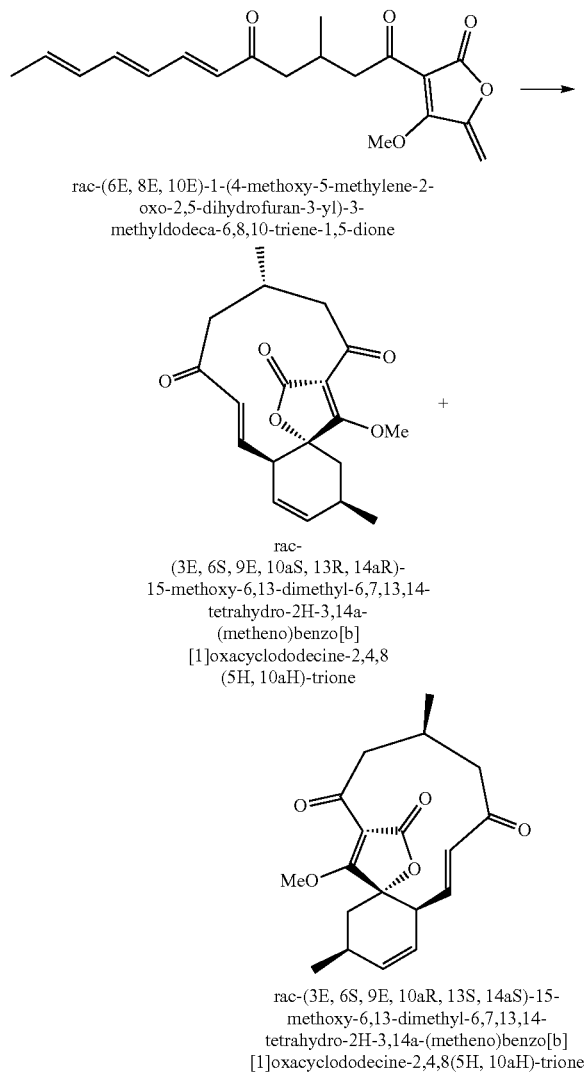

Then macrocyclic substrate rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione was dissolved in 700 equivalents from a 1:2.5 mixture of H₂O:CH₃CN and stirred at room temperature (RT) for one day. The aqueous layer was extracted with dichloromethane three times (DCM (3×)). The combined organic extracts were dried, filtered, and concentrated. More specifically, macrocyclic substrate rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione (17 mg, 0.05 mmol) was dissolved in H₂O (0.5 mL) and CH₃CN (0.2 mL) and stirred at RT for one day. The aqueous layer was extracted with DCM (3×1 mL). The combined organic extracts were dried over MgSO₄, filtered, and concentrated in vacuo, or under vacuum. The crude material was purified by flash column chromatography (20% ethyl acetate:petroleum ether, (EtOAc:PE)) to give hydration adduct rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate (17 mg, 98% yield) as a yellow-orange oil; X-ray crystal structure of rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate was obtained following crystallisation by vapour diffusion of diethyl ether/heptane (Et₂O/heptane). The production of hydration adduct rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate is represented by the following general scheme:

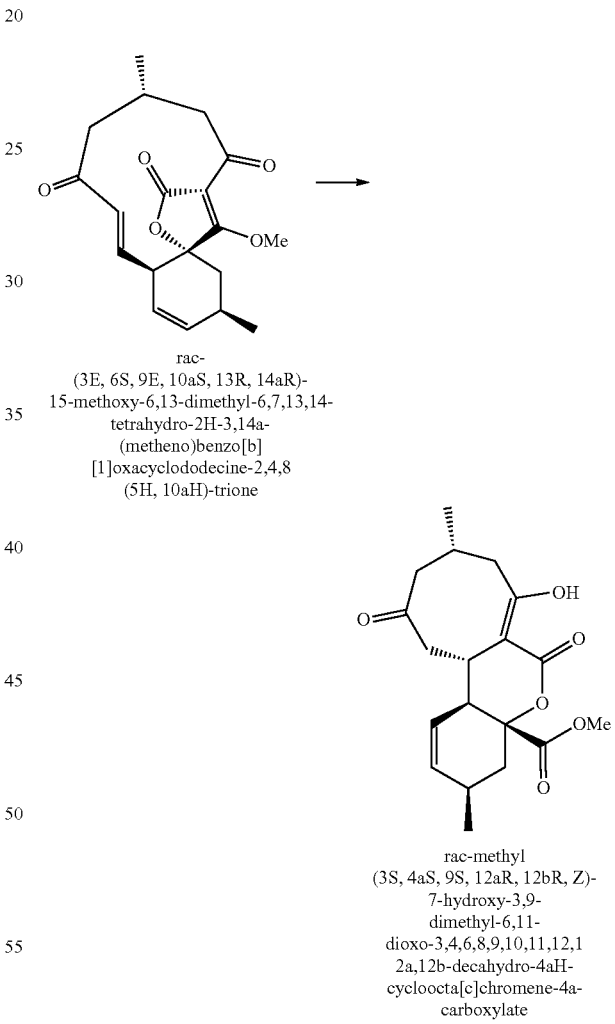

The rearrangement to form rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate results from reacting rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione in an aqueous medium, where water is the main reagent for this transformation, and acetonitrile (MeCN) is used to improve rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione solubility in water.

In an embodiment, the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue of the present subject matter, may be effective in a pharmaceutical or drug composition. Since abyssomicins are a family of spirotetronate natural products exhibiting promising bioactivities, the abyssomicin's biological activities inspire possible applications in medicinal chemistry and drug discovery for the unique structure. The chemical structures of synthesizing substrate analogues are of interest because of their stability for a long time with quite rigid structures, which can be of interest to medicinal chemists and pharmaceutical scientists.

An embodiment of the present subject matter is directed to a pharmaceutical composition comprising the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue and a pharmaceutically acceptable carrier.

An embodiment of the present subject matter is directed to a method of making a pharmaceutical composition including mixing the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue with a pharmaceutically acceptable carrier. For example, the method of making a pharmaceutical composition can include mixing the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue under sterile conditions with a pharmaceutically acceptable carrier with preservatives, buffers, and/or propellants to create the pharmaceutical composition.

An embodiment of the present subject matter is directed to a pharmaceutical composition including the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue. To prepare the pharmaceutical composition, the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue, as an active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral, parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the rac-methyl(3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue or an amount effective to treat a disease, such as a disease associated with those positively treated by the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue, may be determined initially from any examples described herein and adjusted for specific targeted diseases using routine methods.

The rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue can be administered to a subject in need thereof. For example, the antioxidant probiotic nanoparticles can be used to treat a subject suffering from a disease associated with any disease treatable by the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue. The disease can be any disease treatable or positively affected by the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue. In certain embodiments, the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue can be used as an antibacterial agent to treat bacterial infections, diseases, or conditions in a subject. In this regard, the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue can be active against Gram-positive bacteria including methicillin-resistant *Staphylococcus aureus* (MRSA).

An embodiment of the present subject matter is directed to a method of treating any disease treatable and/or positively affected by the rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue, comprising administering to a subject in need thereof a therapeutically effective amount of the pharmaceutical composition according to the present subject matter.

The rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate abyssomicin analogue or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

It is to be understood that the compounds and methods as described herein are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An organic abyssomicin analogue compound rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate having the following structure

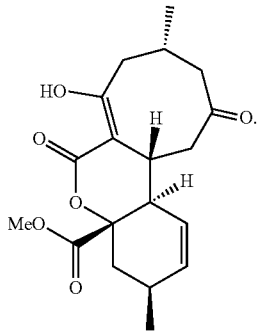

2. A method of synthesizing an organic abyssomicin analogue compound rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate having the following structure

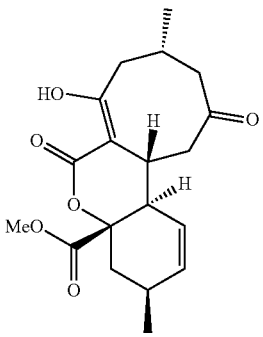

the method comprising the steps of:
dissolving substrate rac-(6E,8E,10E)-1-(4-methoxy-5-methylene-2-oxo-2,5-dihydrofuran-3-yl)-3-methyldodeca-6,8,10-triene-1,5-dione having the following structure

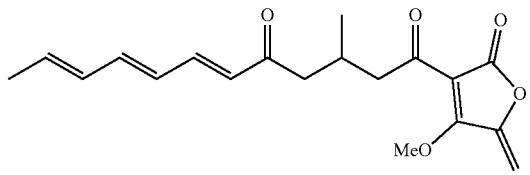

rac-(6E,8E,10E)-1-(4-methoxy-5-methylene-2-oxo-2,5-dihydrofuran-3-yl)-3-methyldodeca-6,8,10-triene-1,5-dione or substrate rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione having the following structure

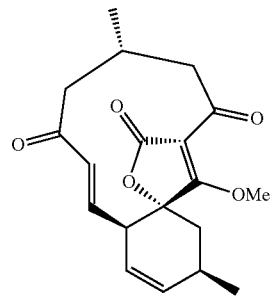

rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione in $H_2O$ and $CH_3CN$ to obtain a first mixture;
stirring the first mixture until reaction completion;
quenching the reaction with organic solvent forming aqueous and organic layers;
extracting the aqueous layer with an organic solvent;
drying, filtering, and concentrating the combined organic extracts to produce a crude material; and
purifying the crude material to obtain hydration adduct rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate.

3. The method of claim 2, wherein the first mixture is stirred at room temperature for about one day.

4. The method of claim 2, wherein the aqueous layer is extracted with dichloromethane.

5. The method of claim 2, wherein the organic extracts are dried over $MgSO_4$, filtered, and concentrated in vacuo.

6. The method of claim 2, wherein the crude material is purified by flash column chromatography (20% ethyl acetate:petroleum ether).

7. The method of claim 6, wherein the hydration adduct rac-methyl (3S,4aS,9S,12aR,12bR,Z)-7-hydroxy-3,9-dimethyl-6,11-dioxo-3,4,6,8,9,10,11,12,12a,12b-decahydro-4aH-cycloocta[c]chromene-4a-carboxylate is obtained at a 98% yield.

8. The method of claim 2, wherein the H$_2$O provides cyclisation followed by hydration.

9. A method of synthesizing rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione having the following structure

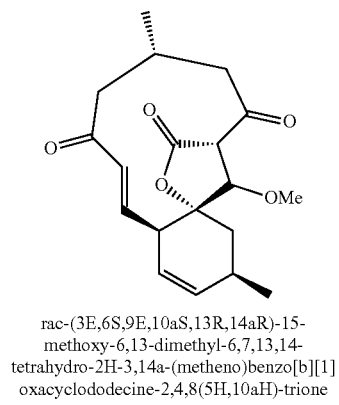 [SMILES: COC1[C@H]2C(=O)C[C@@H](C)CC(=O)/C=C/[C@@H]3C=C[C@H](C)C[C@]13OC2=O]

rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione the method comprising the steps of:

dissolving diketone rac-(6E,8E,10E)-1-(4-methoxy-5-methylene-2-oxo-2,5-dihydrofuran-3-yl)-3-methyl-dodeca-6,8,10-triene-1,5-dione in CHCl$_3$ to produce a reaction mixture;

purifying the reaction mixture to obtain a mixture of diastereomers rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione and rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione;

separating the mixture of diastereomers rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione and rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione;

isolating minor isomer rac-(3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione; and isolating major isomer rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione, wherein the synthesis of rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione is represented by the following general reaction:

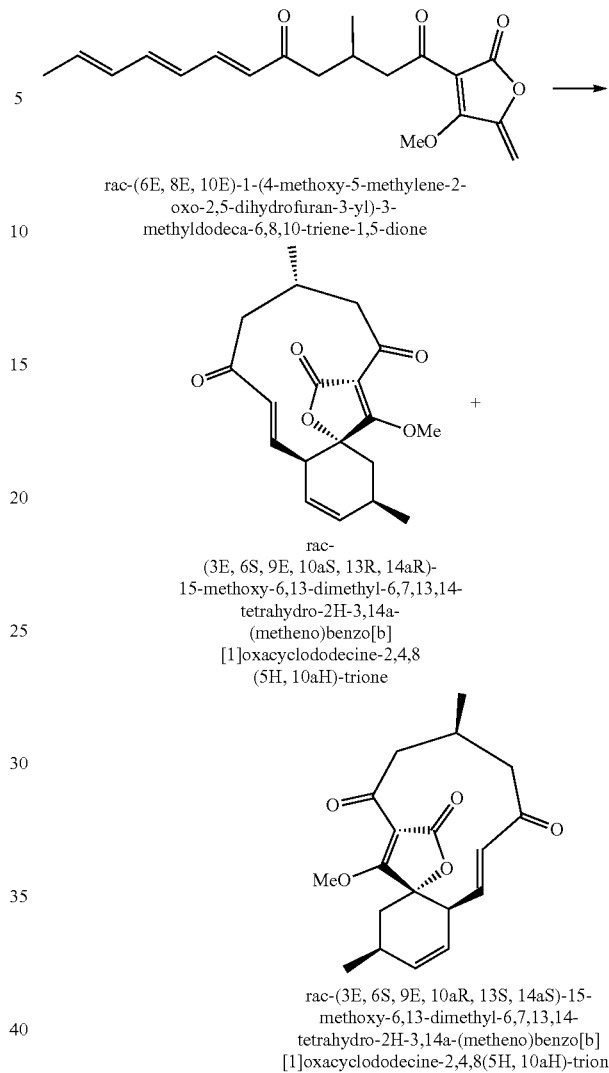

10. The method of claim 9, wherein the dissolved diketone rac-(6E,8E,10E)-1-(4-methoxy-5-methylene-2-oxo-2,5-dihydrofuran-3-yl)-3-methyldodeca-6,8,10-triene-1,5-dione in CHCl$_3$ is refluxed for about 2 days.

11. The method of claim 9, wherein the reaction mixture is purified by flash column chromatography.

12. The method of claim 9, wherein the mixture of diastereomers rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione and (3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione are separated by HPLC.

13. The method of claim 9, wherein the minor isomer (3E,6S,9E,10aR,13S,14aS)-15-methoxy-6,13-dimethyl-6,7,13,14-tetrahydro-2H-3,14a-(metheno)benzo[b][1]oxacyclododecine-2,4,8(5H,10aH)-trione was isolated at a 20% yield.

14. The method of claim 9, wherein the major isomer rac-(3E,6S,9E,10aS,13R,14aR)-15-methoxy-6,13-dimethyl-6,7,13,14-tetrahydro-2H-3,14a-(metheno)benzo[b][1]oxacyclododecine-2,4,8(5H,10aH)-trione was isolated at a 67% yield.

* * * * *